United States Patent [19]

Rohrbach et al.

[11] Patent Number: 4,511,654

[45] Date of Patent: Apr. 16, 1985

[54] PRODUCTION OF HIGH SUGAR SYRUPS

[75] Inventors: Ronald P. Rohrbach, Forest Lake, Ill.; Mary J. Maliarik, Ann Arbor, Mich.; Thomas P. Malloy, Lake Zurich, Ill.

[73] Assignee: UOP Inc., Des Plaines, Ill.

[21] Appl. No.: 499,652

[22] Filed: May 31, 1983

Related U.S. Application Data

[63] Continuation-in-part of Ser. No. 360,120, Mar. 19, 1982, abandoned.

[51] Int. Cl.³ .................... C12P 19/22; C12P 19/20; C12N 11/14
[52] U.S. Cl. ........................... 435/95; 127/55; 210/651; 210/654; 435/96; 435/176
[58] Field of Search ............ 210/653, 654, 655, 500.2, 210/651; 127/54, 55; 435/95, 96, 99, 105; 735/176

[56] References Cited

U.S. PATENT DOCUMENTS

| | | | |
|---|---|---|---|
| 3,331,772 | 7/1967 | Brownscombe et al. | 210/653 |
| 3,720,583 | 3/1974 | Fisher | 435/95 |
| 3,783,100 | 1/1974 | Larson et al. | 435/96 |
| 3,857,782 | 12/1974 | Crowley | 210/646 |
| 4,039,440 | 8/1977 | Cadotte | 210/500.2 |
| 4,338,398 | 7/1982 | Yoneyama | 435/96 |
| 4,376,707 | 3/1983 | Lehmann | 210/679 |
| 4,429,122 | 1/1984 | Zupancic | 536/124 |

FOREIGN PATENT DOCUMENTS 55-141171  11/1980  Japan .................. 210/653

*Primary Examiner*—Peter Hruskoci
*Attorney, Agent, or Firm*—James R. Hoatson, Jr.; Raymond H. Nelson; William H. Page, II

[57] ABSTRACT

The preparation of syrups which contain a high glucose or maltose content may be effected in a two-step process. In the first step, a feedstock such as starch which has been pretreated with alpha-amylase to adjust the dextrose equivalent is contacted with an enzyme such as amyloglucosidase or beta-amylase immobilized on a solid support. The contact time is adjusted by correlating the residence time and the liquid hourly space velocity so as to provide a conversion percentage of starch in the range of from about 50% to 85%, thus avoiding the formation of undesired conversion products. The partially hydrolyzed reaction mixture from the enzyme treatment is then passed through an ultrafiltration membrane whereby the permeate comprising the high glucose or maltose content is recovered, while the retentate is recycled for admixture with the partially hydrolyzed reaction mixture or for further treatment with the immobilized enzyme.

9 Claims, No Drawings

PRODUCTION OF HIGH SUGAR SYRUPS

CROSS-REFERENCE TO RELATED APPLICATION

This application is a continuation-in-part of our co-pending U.S. application Ser. No. 360,120 filed Mar. 19, 1982 and now abandoned, all teachings of which are incorporated herein by reference thereto.

BACKGROUND OF THE INVENTION

In many commercial enterprises, sugar is utilized to a great extent for its sweetening properties. It is used in the sweetening of foods, for the manufacture of syrups and confectionery items, in preserves and jams, as a chemical intermediate for detergents, emulsifying agents and other sucrose derivatives such as plasticizers, resins, glues, etc. The usual derivation of sugar is from cane sugar and sugar beets. It is obtained by crushing and extracting the sugar from the cane with water or extracting the sugar from the sugar beet with water followed by evaporation and purifying with lime, absorbent carbon and/or various liquids. The chief component of this type of sugar is sucrose, while other sugars may contain other polysaccharides such as dextrose and levulose (fructose). Other polysaccharides which possess sweetening properties include glucose, maltose, etc. The various polysaccharides possess varying degrees of sweetness, especially when in pure form and not contaminated by an reversion products.

One source of glucose which possesses a relatively high degree of sweetness and which, in turn, may be converted to fructose, the latter possessing an even greater degree of sweetness, is a starch. As is well known, starch is present in many naturally occurring plants including corn, potatoes, rice, tapioca, wheat, etc. Heretofore, it has been known to treat starch with an enzyme such as amyloglucosidase to obtain glucose. However, the treatment heretofore provided entailed a relatively long residence time in order to obtain a glucose syrup which contained about 94% glucose. The relatively long residence time which has heretofore been required restricts the throughput of glucose and results in the appearance of reversion products which impart a bitter taste to the glucose, thus negating the sweetening property of the compound as well as requiring further treatment in order to remove the offending product. One such reversion product which imparts a bitter taste comprises isomaltose.

Many methods involving the use of an enzyme such as amyloglucosidase to convert starch into sugar have been tried. However, each of these methods has some disadvantages attached thereto. For example, when using a free enzyme, it is necessary to continuously replace the enzyme which is lost during the production of the desired saccharide. Likewise, when using an immobilized enzyme, the heretofore relatively long residence time has resulted in the appearance of unwanted side products.

As will hereinafter be shown in greater detail, we have now discovered that the feedstream comprising a starch which possesses a low dextrose equivalent may be subjected to a partial hydrolysis to provide a predetermined degree of conversion due to a correlation of residence time and liquid hourly space velocity, and to a degree wherein the reversion products which constitute an undesired side reaction are extremely low or, in some instances, non-existent.

BRIEF SUMMARY OF THE INVENTION

This invention relates to a process for obtaining a high glucose or maltose content syrup. More specifically, the invention is concerned with a process for the production of a high glucose or maltose content syrup by treating a feedstock comprising starch with an immobilized enzyme followed by passage of the partially hydrolyzed reaction mixture through an ultrafiltration membrane whereby the permeate which is recovered comprises a syrup having a high glucose or maltose content.

Syrups which are high in glucose or maltose concentration comprise desirable chemical entities. By utilizing these syrups which are high in glucose or maltose content for sweetening processes such as in baking goods, candies or in the case of maltose, in culture media or even as a sweetener or nutrient, it is possible to utilize lesser amounts of these syrups, thereby concomitantly reducing the overall cost of the finished product. In addition, as will hereinafter be set forth in greater detail, the syrups which are high in glucose or maltose content will also contain a relatively small amount or no amount at all of reversion products which impart a bitter taste to the syrup, thereby reducing the efficiency of the glucose or maltose to act as a sweetening agent.

It is therefore an object of this invention to provide a process for producing syrups which possess a high glucose or maltose content.

A further object of this invention is to provide a process for producing syrups which possess a high glucose or maltose content with little or no reversion products present in said syrups.

In one aspect, an embodiment of this invention resides in a process for the production of a high glucose or maltose syrup which comprises treating a feedstock having a low dextrose equivalent with an immobilized enzyme selected from the group consisting of amyloglucosidase and beta-amylase in a conversion zone at conversion conditions adapted to effect a conversion of said feedstock to glucose or maltose in a range of from about 50% to about 85%, passing the resultant partially hydrolyzed reaction mixture through an ultrafiltration membrane to form a retentate and a permeate, recycling the retentate for further conversion, and recovering the permeate comprising a high glucose or maltose content syrup.

A specific embodiment of this invention is found in the process for the production of a high glucose syrup which comprises treating a feedstock comprising starch which has been pretreated with alpha-amylase to provide a dextrose equivalent in the range of from about 5 to about 25 with an amyloglucosidase enzyme composited on a solid support at a temperature in the range of from about 45° to about 70° C., a pressure in the range of from about 1 to about 1000 pounds per square inch, a liquid hourly space velocity in the range of from about 2 to about 50 and for a residence time in a range of from about 4 minutes to about 1.6 hours, passing the resultant partially hydrolyzed reaction mixture through an ultrafiltration membrane comprising polystyrenesulfonate at a temperature in the range of from about ambient to about 70° C. and a pressure in the range of from about 25 to about 1500 pounds per square inch, recycling the retentate material for further conversion and recovering the permeate comprising a syrup possessing a high glucose content.

Other objects and embodiments will be found in the following further detailed description of the present invention.

DETAILED DESCRIPTION OF THE INVENTION

As hereinbefore set forth, the present invention is concerned with a two-step process for the production of syrups which possess a high glucose or maltose content. The process is effected by treating a feedstock, comprising a liquified starch which itself has been pretreated to adjust the dextrose equivalent, with an appropriate enzyme which is in an immobilized state followed by passage of partially hydrolyzed reaction mixture over a membrane, the latter or second step of the process permitting the permeation of the desired sugar through the membrane while concurrently rejecting the higher oligosaccharides which, in the form of the retentate, may be recycled for further treatment with the enzyme.

Heretofore, in order to achieve a syrup which would contain about 94% glucose or maltose by treating starch with an enzyme, it was necessary that the starch be in contact with the enzyme for a relatively long residence time. A disadvantage in allowing the starch to be in contact with the enzyme restricted the throughput of the desired sugar such as glucose or maltose and, when utilizing an immobilized enzyme, the amount of undesired reversion products which possessed a bitter taste would be promoted. For example, isomaltose which possesses a disagreeable taste would be present in the reaction mixture to such an extent as to seriously impair the use of the desired product as a sweetening agent.

As will hereinafter be shown in greater detail, by utilizing the process of the present invention, it is possible to obtain a syrup which contains a high glucose or maltose content, that is, in excess of 94% with little or no reversion products imparting a disagreeable taste to the finished product.

The present process involves the treatment of a feedstock comprising a liquified starch which has been pretreated with an enzyme such as alpha-amylase whereby the dextrose equivalent is increased to a range of from about 5 to about 25. The treatment of the pretreated liquified starch with an immobilized enzyme such as amyloglucosidase or beta-amylase is effected under conversion conditions which will permit a conversion of the feedstock to glucose or maltose in a range of from about 50% to about 85%. The conversion conditions include a temperature in the range of from about 45° to about 70° C. and a pressure in the range of from about 1 to about 1000 pounds per square inch (psi). The residence time during which the starch is in contact with the immobilized enzyme is relatively short, that is, in a range of from about 4 minutes to about 1.6 hours and is in correlation with liquid hourly space velocities which may range from about 2 to about 50.

The space velocity and residence time are correlated in such a manner, i.e., short residence time and high space velocity within the ranges hereinbefore set forth so as to provide a conversion rate within the desired range. Conversely, it is also contemplated that long residence times and low space velocities with the aforesaid range may also be employed to effect the desired result.

The correlation of the space velocity and the relatively short residence time will permit a sufficient conversion of the starch to glucose or maltose within the desired range while preventing the formation of the undesired reversion products to a degree wherein they are extremely low or even in some cases nonexistent. In addition, the relationship between the residence time and the conversion will result in a bimodal reaction product, that is, the molecule sizes will be greatly different. As will hereinafter be shown in greater detail, there is a relatively large difference in size between the glucose or maltose molecules and the remaining oligosaccharides. This difference will permit the use of ultrafiltration membranes to readily separate the permeate from the retentate.

The partially hydrolyzed reaction mixture which is obtained from the conversion step is then subjected to an ultrafiltration step wherein said reaction mixture is passed over a membrane which possesses an appropriate molecular weight and pore sizes whereby the higher glucose syrup will pass through the membrane as permeate while the retentate material containing unhydrolyzed oligosaccharides may be recycled for additional treatment. The ultrafiltration step in the present process may be effected under conditions which will include a temperature in the range of from about ambient (20°–25° C.) up to about 70° C. and a pressure in the range of from about 25 to about 1500 psi.

As heretofore set forth, the enzymes which are utilized in the process of this invention comprise amyloglucosidase or betaamylase which are composited on a solid support. By utilizing enzymes which are immobilized on the support, it is possible to stabilize the enzyme in a relative manner and therefore to permit the reaction of the enzyme which otherwise may be lost in the reaction medium. Such immobilized or insolubilized enzymes may be employed in various reactor systems such as in packed columns, stirring tank reactors, etc., depending upon the nature of the substrate which is utilized therein. By permitting the reuse of the enzymes which are in a relatively stable condition and thus may be utilized for a relatively lengthly period of time, it is possible to operate the process in a commercially attractive and economical manner.

The particular enzyme may be immobilized on a solid support in any manner known in the art. One such method of immobilizing the enzyme which may be used as an illustration of a method for immobilizing the enzyme comprises treating an inorganic porous support material including, but not limited thereto, metal oxides such as alumina, and particularly gamma-alumina, silica, zirconia, silica-magnesia, silica-zirconia-alumina, etc., gamma-alumina containing other inorganic compounds such as boron phosphate, etc., ceramic bodies, ceramic fibers, ceramic monoliths which may be coated with a porous inorganic oxide, as well as compositions of the aforementioned materials, one of said materials which may serve as a coating for another material comprising the solid support. The service area of the particular porous support may vary over a relatively wide range, said range being from about 1 to about 500 or more $m^2/g$. In addition, the configuration of the support material may vary depending upon the particular type of support which is utilized. For example, the support may be in the form of spheres, particulates, monoliths, pellets, fibers, etc. It is to be understood that the aforementioned types of porous supports and configurations thereof are given merely for purposes of illustration and it is not intended that the supports are limited thereto.

In one method of preparation, the porous support material will be treated with a solution, preferably aqueous in nature, of a polyfunctional monomer, a low molecular weight polymer, a polymer hydrolysate, or a preformed polymer, following which the unadsorbed solution is removed by any means known in the art such as draining, etc. It is also contemplated that other inexpensive organic solvents such as acetone, methanol, tetrahydrofuran, etc., may also be used as the carrier for the aforementioned initially added polyfunctional monomers or polymers. Following the removal of the unadsorbed solution, the wet porous support is then contacted with a sufficiently large excess of a second bifunctional monomer of from about 3 to about 50 or more mole proportions, relative to the initial additive which reacts therewith to provide pendant groups extending from the resulting copolymer containing unreacted terminal functional moieties. The reactive groups of the bifunctional monomer are preferably separated by a chain containing from about 4 to about 10 carbon atoms, which also may be a cyclic as well as a straight chain. This second bifunctional monomer will also be added preferably in an aqueous solution, whereby the copolymer which is both entrapped and also adsorbed in part in the pores of the inorganic support will be formed and from which pendant groups of the second monomer will extend. These pendant groups will contain unreacted terminal functional moieties due to the fact that a sufficient excess amount of the second bifunctional monomer was employed in treating the organic polymeric material originally adsorbed on the support. The unreacted functional moieties are then available for covalent binding to the enzyme, which is added to the resulting organic-inorganic matrix, again usually in an aqueous solution. After removal of the unreacted materials by conventional means such as by treating, washing, etc. the enzyme covalently bound to the pendant functionalized groups remains attached at the terminal portions thereof. It is therefore readily apparent that the entire immobilization procedure can be conducted in a simple and inexpensive manner, for example, in a column packed with the inorganic supports, utilizing an aqueous or inexpensive solvent media, the procedure being conducted over a temperature differential which may range from subambient (about 5° C.) up to elevated temperatures of about 60° C., and preferably at ambient (about 20°–25° C.) temperature, said procedure being effected by utilizing a minimum of operating steps and, in addition, permitting a ready recovery of the excess reactants, unbound enzyme and finished composition of matter of which the former may be reused.

The copolymeric materials which are formed in situ in such a manner so that the copolymeric material is both entrapped and also adsorbed in part in the pores of the inorganic support of the type hereinbefore set forth may be produced according to the general methods hereinbefore described, that is, by first adsorbing a solution containing from about 2 to about 50% of a polyfunctional monomer, polymer hydrolysate, or a preformed polymer, including low molecular weight forms thereof, these polymeric additives being synthetic or naturally occurring in origin, and which are preferably soluble in water or other solvents which are inert to the reactions subsequently employed. As hereinbefore set forth, it is contemplated that a second bifunctional monomer is then added in a similar manner in solution to form an organic-inorganic matrix by further reaction with the original polyfunctional additive adsorbed on the inorganic support to produce a copolymer which may also be cross-linked. The second bifunctional monomer reactant is present in an excess as needed to produce pendant terminally functionalized groups in the range of from about 2 to about 50 moles or more of bifunctional monomer per mole of monomer, hydrolyzed polymer or preformed polymer adsorbed on the inorganic support. The amount of the first monomer, etc. which is adsorbed on the support will depend on many variables including the type of porous support, the pH of the solution in which it is dissolved, the concentration of the material which is present, as well as reaction parameters including temperature, pressure, etc. While the excess of the second bifunctional monomer may range from about 2 to about 50 moles or more per mole of the original additive, etc., it is usually satisfactory that the excess be in the range of from about 4 to about 25 moles of bifunctional monomer. The unreacted excess monomer may be readily recovered for reuse as well as the unadsorbed polymeric material originally added to the support.

The functional groups which are present on the bifunctional monomer will comprise well-known reactive moieties such as amino, hydroxyl, carboxyl, thiol, carbonyl, etc., moieties. As was also hereinbefore set forth, the reactive groups of the bifunctional compounds are preferably, but not necessarily, separated by chains containing from about 4 to about 10 carbon atoms. The reactive moieties are capable of covalently bonding with both the initial additives and subsequently, after washing out unreacted materials, with the enzyme which is to be added in a subsequent step, said enzyme being then covalently bound to the functional group at the terminal portion of the pendant chain. After addition of the enzyme to this composition, a relatively stable enzyme conjugate will be produced which possesses high activity and high stability. The unadsorbed enzyme can also be recovered for reuse.

Specific examples of polyfunctional monomers, low molecular weight polymers, polymer hydrolysates or preformed polymers which may be initially adsorbed on the inorganic support will include water soluble polyamines such as ethylenediamine, diethylenetriamine, triethylenetetramine, tetraethylenepentamine, pentaethylenehexamine, hexamethylenediamine, polyethyleneimine, etc.; water insoluble but solvent or aqueous acid soluble polyamines such as methylenedicyclohexylamine, methylenedianiline, etc., and natural and synthetic, partially hydrolyzed polymers and preformed polymers, soluble in either aqueous or solvent media, such as partially hydrolyzed Nylon, collagen, polyacrolein, polymaleic anhydride, alginic acid, casein hydrolysate, gelatin, etc. Some specific examples of intermediate bifunctional monomeric materials which may be added to the above enumerated products in an excess in the range hereinbefore set forth to produce an organic-inorganic matrix and which possess the necessary characteristics hereinbefore set forth include compounds such as glutaraldehyde, adipoyl chloride, sebacoyl chloride, toluene diisocyanate, hexamethylenediisocyanate, terephthalic diesters or acyl halides, etc. Due to the large excess of intermediary, or spacer, bifunctional monomeric molecules which are used, the polymeric matrix which is formed will contain pendant groups comprising the spacer molecules, said molecules extending from the matrix and having reactive moieties available at the terminal portions thereof which are capable of reacting with and binding the enzyme to the spacer molecules via covalent bonds. Therefore, it is readily apparent that a suitable organic-inorganic matrix which is applicable in many situations will be formed with the support material by adsorbing any of the type of materials hereinbefore described which are known to the art and then treated with any bifunctional monomer molecule which is also known to the art and is suitably functionalized to react with the original additive, provided that a large enough excess of the bifunctional molecule is used to provide pendant groups which are capable of subsequently reacting with the enzyme which is desired to be immobilized. By utilizing these functional pendant groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or crosslinkage of the enzyme with adjacent enzyme molecules by means of bifunctional reagents, etc. Not all formulations, however, will produce equivalent results in terms of stability or activity.

To form an immobilized enzyme conjugate or system, an aqueous solution of amyloglucosidase or beta-amylase is contacted with or recycled over the treated support material which contains the polymeric material to effect a covalent bonding of enzyme to the terminal aldehydic groups of functionalized moieties which extend from the support matrix. This occurs until there is no further covalent bonding of the enzymes to the pendant molecules. Any excess enzyme is recovered by draining and washing the conjugate to thus prepare an immobilized enzyme system for use in the process of the present invention.

It is contemplated within the scope of this invention that the ultra-filtration membranes which are used to recover a syrup containing a high glucose or maltose content from the partially hydrolyzed reaction mixture resulting from the treatment of a liquid starch feedstock with an immobilized enzyme may comprise any membrane which possesses an appropriate molecular weight as well as pore sizes capable of yielding the desired high glucose or maltose content as the permeate while retaining the rejected material which contains unhydrolyzed oligosaccharides. In the preferred embodiment, the ultrafiltration membrane will possess a molecular weight cut-off in the range of from about 100 to about 5000 and will also possess pore sizes in the range of from about 5 to about 125 angstroms. Some specific examples of these membranes which may be utilized will include cellulose acetates such as cellulose diacetate, cellulose triacetate or mixtures thereof, a membrane resulting from polyethyleneimine cross-linked with a dialdehyde, a diacidchloride, or a diisocyanate, polyacrolein, chitosan cross-linked with a dialdehyde such as glutaraldehyde, polystyrenesulfonates, etc. It is to be understood that these ultra-filtration membranes are only representative of the class of membranes which may be employed and that the present invention is not necessarily limited thereto.

The two-step process of the present invention may be effected in any suitable manner and may comprise either a batch or continuous type operation. For example, when a batch type operation is employed, a quantity of the feedstock comprising a liquid starch which has been previously treated with alpha-amylase to increase the dextrose equivalent is contacted with an immobilized amyloglucosidase, in the event that a syrup high in glucose content is desired, for a predetermined period of time while employing reaction conditions which include a temperature of from about 45° to about 70° C. and a pressure which may range from about 1 to about 1000 psi. In addition, the residence time during which the feedstock is in contact with the immobilized enzyme is correlated with the liquid hourly space velocity at which the feed is introduced so as to produce a conversion of the liquid starch to glucose within the desired range. After passage over the immobilized enzyme, the effluent is recovered and the partially hydrolyzed starch is then subjected to an ultrafiltration step. In this step, the reaction mixture is passed through an ultrafiltration membrane of the type hereinbefore set forth whereby the permeate which possesses a high glucose or maltose content is recovered as the permeate upon separation from the retentate. The latter may then also be recycled, a portion of the recycle stream being admixed with the effluent from the enzyme treatment while another portion of the retentate is admixed with the feed stream to the immobilized enzyme treatment zone. It is also contemplated that a third portion, if so desired, may be recycled back to the zone in which the feedstock is pretreated with alpha-amylase.

It is also contemplated within the scope of this invention that the process may be effected in a continuous manner of operation. When this type of operation is employed, the feedstock comprising the treated liquified starch is continuously charged to a reaction vessel such as a column which contains the desired immobilized enzyme, said column being maintained at the proper operating conditions of temperature and pressure. After passage over the enzyme at a predetermined liquid hourly space velocity which is sufficiently high so as to only partially hydrolyze the feedstock, with a concomitant low or nonexistent production of reversion products such as isomaltose, the effluent is continuously withdrawn and charged to an ultrafiltration apparatus which contains a membrane of the type hereinbefore set forth. After passage through this apparatus, which is also maintained at the proper operating conditions of temperature and pressure, the permeate comprising a syrup which has a high glucose or maltose content, i.e., above 94%, is recovered. The retentate material which contains unhydrolyzed oligosaccharides such as those which have a DP rating of $DP_7$, $DP_8$, $DP_{9+}$ (the designation DP being the degree of polymerization) is also recovered and a portion thereof recycled back to the column containing the immobilized enzyme for further use as a portion of the feedstock, another portion admixed with the effluent from the immobilized enzyme treatment and, if so desired, a portion to the alpha-amylase step for pretreatment.

The following examples are given for the purpose of illustrating the present invention. However, it is to be understood that these examples are given merely for purposes of illustration and that the present process is not necessarily limited thereto.

EXAMPLE I

To illustrate the process of the present invention in which the object is to recover a syrup which contains a high glucose or maltose content, a starch feedstock was treated with alpha-amylase to adjust the dextrose equivalent to 15 DE. In this case, the immobilized enzyme comprised amyloglucosidase composited on a solid alumina support which had been treated with polyethyleneimine and glutaraldehyde in a manner hereinbefore set forth in the specification to provide an organic-inorganic matrix containing pendant aldehydic moieties. The treated starch feedstock was passed through a column of 40 cc of the immobilized enzyme, said starch feedstock containing 0.1% benzoate and 50 ppm of sodium omadine at a pH of 4.2. The starch was treated at a temperature of 45° C., and a pressure greater than atmospheric at a liquid hourly space velocity of 3.21. The effluent from this column was analyzed by means of liquid chromatography. The analysis showed the following area % in which DP is the degree of polymerization (for example, $DP_7$=seven (7) monomers of glucose in the oligosaccharide):

| $DP_{9+}$ | $DP_8$ | $DP_7$ | $DP_6$ | $DP_5$ | $DP_4$ | $DP_3$ | $DP_2$ | Glucose |
|---|---|---|---|---|---|---|---|---|
| 19.1 | 0.2 | 0.1 | — | — | — | 0.3 | 3.1 | 77.2 |

The effluent in an amount of 200 cc which was recovered from this column was then passed through a cellulose acetate membrane, 130.7 cc out of the original 200 cc being obtained and constituting the permeate. Analysis of the permeate after passage through the membrane at a temperature of 22° C. and a pressure of 90 psi showed that said permeate contained 94.2% glucose, 3.6% maltose and only 1.7% of the oligosaccharides having a DP of 9+.

The retentate which is recovered from the treatment with the cellulose acetate membranes may then be recycled and utilized as a portion of the feedstock which is charged to the zone containing the immobilized enzyme comprising amyloglucosidase composited on the treated alumina support.

EXAMPLE II

In a manner similar to that hereinbefore set forth in Example I, a treated liquified starch feedstock was again passed through an immobilized amyloglucosidase column under conditions similar to those in Example I. The effluent from this column, which contained 77.2% glucose as well as minor amounts of maltose, $DP_3$, $DP_7$, $DP_8$ and a major amount of $DP_{9+}$ oligosaccharides, was passed through a membrane comprising polystyrenesulfonate and sold under the trade name Amicon UM2. The volume of the effluent which passed through the membrane was 122.8 cc. Analysis of the permeate by means of liquid chromatography showed 97.6% glucose, 2.3% maltose, and only 0.1% of $DP_{9+}$ oligosaccharides.

When the above experiment was repeated using a membrane comprising cellulose acetate sold under the trade name Nuclepore and the effluent from the immobilized amyloglucosidase column was passed over this membrane at a temperature of 22° C. and a pressure of 90 psi, the permeate was found to contain 97.5% glucose, 2.3% maltose, and 0.2% $DP_{9+}$ oligosaccharides.

Likewise, the retentate which may be recovered from the treatment of the effluent with the cellulose acetate membrane may be recovered and recycled, a portion of the retentate being admixed with the effluent from the immobilized enzyme treatment while the other portion is recycled to form a portion of the feedstock which is charged to the immobilized enzyme treatment zone.

EXAMPLE III

To illustrate the ability of the process of the present invention to recover a product containing a high maltose concentration, a liquified starch feedstock which had been pretreated with alpha-amylase to adjust the dextrose equivalent to the desired level was passed through a column containing 100 cc of beta-amylase immobilized on a solid matrix similar to that set forth in Example I above. The feedstock which had a pH of 5.0 contained 0.1 mole of acetate and 0.2 mole of benzoate which acted as a buffer. The feedstock was passed over the enzyme at a temperature of 55° C., a pressure greater than atmospheric, at a liquid hourly space velocity of 5. The effluent which was recovered from this column was subjected to liquid chromatography analysis with the following result:

| HPLC ANALYSIS: (AREA %) | | | | | | | | |
|---|---|---|---|---|---|---|---|---|
| $DP_{9+}$ | $DP_8$ | $DP_7$ | $DP_6$ | $DP_5$ | $DP_4$ | $DP_3$ | $DP_2$ | Glucose |
| 36.9 | 0.9 | 0.3 | 0.3 | 0.1 | 0.5 | 11.1 | 50.2 | .5 |

The effluent from this column in an amount of 100 cc was passed through a cellulose acetate membrane while maintaining the membrane apparatus at a temperature of 22° C. and a pressure of 90 psi. Analysis of the permeate by means of liquid chromatography showed the presence of 79.0% maltose, 16.3% of a $DP_3$ product and 2.4% of a $DP_{9+}$ oligosaccharide.

When the above experiment was repeated using an ultrafiltration membrane sold under the trade name of Amicon UM2, the permeate was found to contain 90.1% maltose, 9.7% of a $DP_3$ oligosaccharide and only 0.2% of a $DP_{9+}$ oligosaccharide.

In a similar manner the retentate which is recovered from the treatment with the ultrafiltration membrane of the above paragraph may be recycled, a portion being admixed with the effluent withdrawn from the treatment with the immobilized beta-amylase while another portion may be admixed with the feedstock comprising the liquified starch prior to passage over the immobilized enzyme.

EXAMPLE IV

In this example, a liquified starch feedstock which may be pretreated with alpha-amylase to adjust the dextrose equivalent of said starch to a predetermined level may be passed through an immobilized amyloglucosidase column at a temperature of 45° C. and a pressure greater than atmospheric. The effluent from the column may be withdrawn after having been in contact with the immobilized enzyme for a predetermined period of time sufficient to permit a conversion to glucose of about 75% and may then be passed through an ultrafiltration membrane comprising polyacrolein, said passage over the membrane being effected at conditions which will include ambient temperature and a pressure of about 25 psi. The permeate may be recovered while the retentate may be recycled to be admixed with the effluent prior to passage over the aforesaid membrane.

In a similar manner, a liquified starch feedstock which contains a dextrose equivalent of about 15 may also be passed over an immobilized enzyme comprising beta-amylase composited on a treated alumina support, the reaction conditions including a temperature of about 50° C. and a pressure greater than atmospheric. After passage over the enzyme at a predetermined liquid hourly space velocity and for a residence time sufficient to permit a conversion of about 75% of the starch to glucose, the effluent may be continuously withdrawn and passed over the membrane comprising polyethyleneimine dialdehyde, said passage over the membrane being effected at a temperature of about 25° C. and a pressure of about 100 psi. The permeate which may contain over 90% glucose may be recovered while the retentate may be recycled, one portion of which may be admixed with the effluent, withdrawn from the enzyme treatment zone, a second portion may be recycled to be admixed with the liquified starch feedstock entering the immobilized enzyme zone, while a third portion may be recycled to the pretreatment zone in which the starch feedstock is contacted with alpha-amylase, the alpha-amylase acting to raise the dextrose equivalent of the starch to a predetermined level.

The effluent which is continuously withdrawn from the treatment with the immobilized enzyme may also be passed over an ultrafiltration membrane comprising chitosan dialdehyde at reaction conditions which include a temperature of about 22° C. and a pressure of about 100 psi, the permeate comprising a major portion of glucose being recovered while the retentate may be recycled to be admixed with the effluent which is dispersed from the immobilized enzyme treatment zone.

We claim as our invention:

1. A process for the production of a high glucose or maltose syrup which comprises treating a feedstock having a low dextrose equivalent in the range of from about 5 to about 25 with an immobilized enzyme selected from the group consisting of amyloglucosidase and beta-amylase attached to an inorganic porous support material in a conversion zone at conversion conditions comprising a temperature in the range of from about 45° to about 70° C., a pressure in the range of from about 1 to about 1000 psi, a Liquid Hourly Space Velocity in the range of from about 2 to about 50 and a residence time in a range of from about 4 minutes to about 1.6 hours to form a partially hydrolyzed reaction mixture by conversion of said feedstock to glucose or maltose in a range of from about 50% to about 85%, while substantially preventing the formation of reversion products which impart a disagreeable taste to said syrup, passing the resultant partially hydrolyzed reaction mixture through an ultrafiltration membrane to form a retentate and a permeate, recycling the retentate to said conversion zone, and recovering the permeate comprising said high glucose or maltose content syrup.

2. The process as set forth in claim 1 in which said partially hydrolyzed reaction mixture is passed through said membrane at a temperature of from about ambient to about 70° C. and a pressure in the range of from about 25 to about 1500 psi.

3. The process as set forth in claim 1 in which said feedstock comprises starch which has been treated with alpha-amylase composited on a solid alumina support.

4. The process as set forth in claim 1 in which said ultrafiltration membrane comprises cellulose acetate.

5. The process as set forth in claim 1 in which said ultrafiltration membrane comprises polyacrolein.

6. The process as set forth in claim 1 in which said ultrafiltration membrane comprises polyethyleneimine dialdehyde.

7. The process as set forth in claim 1 in which said ultrafiltration membrane comprises polystyrenesulfonate.

8. The process as set forth in claim 1 in which said immobilized enzyme comprises amyloglucosidase composited on a solid alumina support.

9. The process as set forth in claim 1 in which said immobilized enzyme comprises beta-amylase composited on a solid alumina support.

* * * * *